(12) United States Patent
Haick et al.

(10) Patent No.: US 9,365,419 B2
(45) Date of Patent: Jun. 14, 2016

(54) METHOD OF DIAGNOSING, PROGNOSING AND MONITORING ALZHEIMER'S DISEASE

(75) Inventors: Hossam Haick, Haifa (IL); Urike Tisch, Haifa (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 920 days.

(21) Appl. No.: 13/424,763

(22) Filed: Mar. 20, 2012

(65) Prior Publication Data

US 2012/0245854 A1    Sep. 27, 2012

Related U.S. Application Data (60) Provisional application No. 61/466,962, filed on Mar. 24, 2011, provisional application No. 61/471,217, filed on Apr. 4, 2011.

(51) Int. Cl.
| | | |
|---|---|---|
| *A61B 5/08* | (2006.01) | |
| *B82Y 5/00* | (2011.01) | |
| *B82Y 15/00* | (2011.01) | |
| *A61B 5/00* | (2006.01) | |
| *G06F 19/00* | (2011.01) | |

(52) U.S. Cl.
CPC . *B82Y 5/00* (2013.01); *A61B 5/082* (2013.01); *A61B 5/4082* (2013.01); *A61B 5/4842* (2013.01); *B82Y 15/00* (2013.01); *G06F 19/707* (2013.01)

(58) Field of Classification Search
CPC combination set(s) only.
See application file for complete search history.

(56) References Cited

U.S. PATENT DOCUMENTS

| | | | |
|---|---|---|---|
| 6,610,270 B1 | 8/2003 | Ajami | |
| 2002/0081745 A1* | 6/2002 | Ross et al. | 436/141 |
| 2010/0273665 A1* | 10/2010 | Haick et al. | 506/8 |
| 2011/0098591 A1* | 4/2011 | Haick et al. | 600/532 |
| 2011/0244584 A1* | 10/2011 | Haick et al. | 436/71 |
| 2011/0269632 A1* | 11/2011 | Haick et al. | 506/7 |

FOREIGN PATENT DOCUMENTS

| | | |
|---|---|---|
| WO | 00/00636 A1 | 1/2000 |
| WO | 00/61002 A1 | 10/2000 |
| WO | 03/094932 A1 | 11/2003 |
| WO | 2005/079669 A1 | 9/2005 |
| WO | 2007/045865 A1 | 4/2007 |
| WO | 2007/086986 A1 | 8/2007 |
| WO | 2008/124187 A1 | 10/2008 |

(Continued)

OTHER PUBLICATIONS

Barash, Orna, et al. "Sniffing the Unique "Odor Print" of Non-Small-Cell Lung Cancer with Gold Nanoparticles." Small 5.22 (2009): 2618-2624 (Barash).*

(Continued)

*Primary Examiner* — Michael Kahelin
*Assistant Examiner* — Mitchell E Alter
(74) *Attorney, Agent, or Firm* — Knobbe, Martens, Olson & Bear, LLP (57) ABSTRACT

The present invention provides a system and method for diagnosing, monitoring or prognosing Alzheimer's disease using at least one sensor comprising carbon nanotubes coated with cyclodextrin or derivatives thereof and/or at least one sensor comprising metal nanoparticles coated with various organic coatings in conjunction with a learning and pattern recognition algorithm.

18 Claims, 3 Drawing Sheets

(56) References Cited

FOREIGN PATENT DOCUMENTS

| WO | 2009/066293 A1 | 5/2009 |
|---|---|---|
| WO | 2009/144725 A1 | 12/2009 |
| WO | 2010/040097 A1 | 4/2010 |
| WO | 2010/064239 A1 | 6/2010 |
| WO | 2010/066000 A1 | 6/2010 |
| WO | 2010/079490 A1 | 7/2010 |
| WO | 2011/010103 A1 | 1/2011 |

OTHER PUBLICATIONS

Ahmed et al., (2009) Metabolic profiling of Parkinson's disease: evidence of biomarker from gene expression analysis and rapid neural network detection. J Biomed Sci 16(1): 63.

Baykal et al., (2008) Aberrant regulation of choline metabolism by mitochondrial electron transport system inhibition in neuroblastoma cells. Metabolomics 4(4): 347-356.

Bogdanov et al., (2008) Metabolomic profiling to develop blood biomarkers for Parkinson's disease. Brain 131(pt 2): 389-96.

Dovgolevsky et al., (2009) Chemically sensitive resistors based on monolayer-capped cubic nanoparticles: towards configurable nanoporous sensors. Small 5(10): 1158-1161.

Greenberg et al., (2009) A proposed metabolic strategy for monitoring disease progression in Alzheimer's disease. Electrophoresis 30(7): 1235-1239.

Hughes et al., (2002) The accuracy of diagnosis of parkinsonian syndromes in a specialist movement disorder service. Brain 125(pt 4): 861-870.

Michell et al., (2008) Metabolomic analysis of urine and serum in Parkinson's disease. Metabolomics 4(3): 191-201.

Quinones and Kaddurah-Daouk (2009) Metabolomics tools for identifying biomarkers for neuropsychiatric diseases. Neurobiol Dis 35(2): 165-176.

Amann, A. et al., (2010) Chapter 7: Methodological issues of sample collection and analysis of exhaled breath. European Respiratory Society Monograph 49:96-114.

Barba, Ignasi et al., (2008) Alzheimer's disease beyond the genomic era: nuclear magnetic resonance (NMR) spectroscopy-based metabolomics. J Cell Mol Med 12(5A):1477-1485 Epub Jun. 28, 2008.

Brust, Mathias et al., (1994) Synthesis of thiol-derivatised gold nanoparticles in a two-phase Liquid-Liquid system. J Chem Soc Chem Commun 1994(7):801-802.

Coelho, Leiliane et al., (2007) Breath air analysis and its use as a biomarker in biological monitoring of occupational and environmental exposure to chemical agents. J Chromatography B 853(1-2):1-9.

Dovgolevsky, Ekaterina and Haick, Hossam (2008) Direct observation of the transition point between quasi-spherical and cubic nanoparticles in a two-step seed-mediated growth method. Small 4(11):2059-2066 Epub Oct. 17, 2008.

Ewers, Michael et al., (2010) Blood-based biomarkers of microvascular pathology in Alzheimer's disease. Exp Gerontol 45(1):75-79 Epub Sep. 24, 2009.

Goetz, Christopher G. et al., (2004) Movement Disorder Society Task Force report on the Hoehn and Yahr staging scale: status and recommendations. Mov Disord 19(9):1020-1028.

Haick, Hossam et al., (2009) Sniffing chronic renal failure in rat model by an array of random networks of single-walled carbon nanotubes. ACS Nano 3(5):1258-1266.

Hoehn, Margaret M. and Yahr, Melvin D. (1967) Parkinsonism: onset, progression and mortality. Neurology 17 (5):427-442.

Hostetler, Michael J. et al., (1998) Alkanethiolate Gold Cluster Molecules with Core Diameters from 1.5 to 5.2 nm: Core and Monolayer Properties as a Function of Core Size. Langmuir 14(1):17-30.

Hu, William T. et al., (2010) Biomarker discovery for Alzheimer's disease, frontotemporal lobar degeneration, and Parkinson's disease. Acta Neuropathol 120(3):385-399 Epub Jul. 22, 2010.

Ionescu, R. et al., (2002) Quantitative analysis of $NO_2$ in the presence of CO using a single tungsten oxide semiconductor sensor and dynamic signal processing. Analyst 127(9):1237-1246.

Ouyang, Gangfeng and Pawliszyn, Janusz (2006) SPME in environmental analysis. Anal Bioanal Chem 386 (4):1059-1073 Epub May 4, 2006.

Peng, Gang at al., (2008) Detecting simulated patterns of lung cancer biomarkers by random network of single-walled carbon nanotubes coated with nonpolymeric organic materials. Nano Lett 8(11):3631-3635 Epub Oct. 8, 2008.

Peng, Gang et al., (2009) Diagnosing lung cancer in exhaled breath using gold nanoparticles. Nat Nanotech 4 (11):669-673.

Peng, G. et al., (2010) Detection of lung, breast, colorectal, and prostate cancers from exhaled breath using a single array of nanosensors. Br J Cancer 103(4):542-551 Epub Jul. 20, 2010.

Zhao, Xiao-Mei et al., (1997) Soft lithographic methods for nanofabrication. J Mater Chem 7(7):1069-1973.

Tisch et al., (2012) Detection of Asymptomatic Nigrostriatal Dopaminergic Lesion in Rats by Exhaled Air Analysis Using Carbon Nanotube Sensors. ACS Chem Neurosci 3(3): 161-166.

\* cited by examiner

METHOD OF DIAGNOSING, PROGNOSING AND MONITORING ALZHEIMER'S DISEASE

FIELD OF THE INVENTION

The present invention relates to a system and methods for diagnosis, prognosis and monitoring of Alzheimer's disease through breath analysis.

BACKGROUND OF THE INVENTION

Alzheimer's disease (AD) is the most common neurodegenerative disease, affecting over 26 million people worldwide. It is a progressive brain disease that is characterized by dementia as well as other cognitive impairments. The neuropathology of AD is attributed to the accumulation of highly insoluble intraneuronal protein aggregates, composed of the protein tau, also known as neurofibrillar tangles (NFT). The current diagnosis of AD mostly relies on clinical symptoms and is associated with highly variable sensitivity and specificity, depending on the proficiency of the treating physician. AD can easily be confused with other neurodegenerative disorders such as Parkinson's disease (PD), which can encompass cognitive abnormalities in addition to the classic PD symptoms. The AD pathology is typically unobserved and can precede the first symptoms, caused by irreversible neuronal damage, by more than a decade.

Currently, no biochemical tests are known for the diagnosis of AD or for monitoring the progression of the disease. AD-characteristic variations in metabolites such as N-acetylaspartate (NAA), 1-(9E-hexadecenoyl)-sn-glycero-3-phosphocholine, D-glucosaminide and compounds that contain cholintrimethylamine and ethanolamines were detected in cerebrospinal fluid (CSF) and other body fluids, but no robust AD biomarkers could yet be established (Hu et al., Acta Neuropathol., 2010, 120, 385-399; Ewers et al., Exp. Gerontol. 2010, 45, 75-79; Barba et al., J. Cell Mol. Med., 2008, 12, 1477-1485; and WO 2007/045865).

WO 2000/000636 discloses a method of determining the in vivo conversion activity of a Class I, II or III gateway enzyme, said method comprising the steps of: identifying a Class I, II or III gateway enzyme to be assayed; selecting a labelled metaprobe for said enzyme, said metaprobe being selected so that when acted upon by said enzyme, at least one labelled end product that is directly detectable is produced; administering to a patient a defined amount of said labelled metaprobe; and determining the extent of conversion of said metaprobe to said labelled end product by said enzyme.

WO 2011/010103 discloses a method for classifying an individual, inter alia for having or having an increased risk of developing a pathological condition including AD, the method comprising assessing any one or more of (a) a bacterial metabolite conjugated to a sulfur-containing moiety (b) a cresol metabolite and (c) overall sulfur concentration and/or distribution of sulfur atoms in molecules in a sample taken from the individual.

WO 2010/066000 discloses a method for predicting the susceptibility of a subject to a mental or neurodegenerative disorder, including AD, the method comprising: (a) obtaining one or more biological samples from the subject; (b) determining the levels of one or more biomarkers in the sample, wherein the biomarkers are selected from pyrroles, histamine, methionine adenosyltransferase (MAT) activity, homocysteine, copper and zinc; and (c) comparing the level (s) of the biomarker(s) determined in (b) with the level(s) of said biomarker(s) from one or more control samples, wherein abnormal levels of the one or more biomarkers in the sample (s) from the subject compared to the one or more control samples is predictive of susceptibility of the subject to a mental or neurodegenerative disorder.

WO 2010/040097 discloses methods and devices for the detection of conditions or disorders including AD by detecting altered levels of stress response pathway biomarkers. Also provided are methods and reagents for identifying panels of biomarkers associated with a condition or disorder.

WO 2009/144725 to one of the inventors of the present application discloses a system for detecting volatile organic compounds derived from a breath sample, the system comprising: (a) an apparatus comprising an array of chemically sensitive sensors of single walled carbon nanotubes coated with non-polar small organic molecules, and (b) a processing unit comprising a learning and pattern recognition analyzer wherein the learning and pattern recognition analyzer receives sensor output signals and compares them to stored data.

WO 2010/064239 to one of the inventors of the present application discloses a system comprising an array of sensors for measuring volatile organic compounds as biomarkers for diagnosis, prognosis and monitoring of renal insufficiencies, the system comprises an array of sensors comprising a (semi-) conductive random network of single-walled carbon nanotubes (SWCNTs) coated with an organic coating which comprises oligomers or polymers modified with at least one polar functional group, in conjunction with learning and pattern recognition algorithms.

WO 2009/066293 to one of the inventors of the present application discloses an apparatus comprising at least one chemically sensitive sensor for detecting volatile and non-volatile compounds, wherein the chemically sensitive sensor comprises cubic nanoparticle conductive cores capped with an organic coating. Methods of use thereof in identifying various disease biomarkers, and in food quality and environmental control are disclosed.

WO 2010/079490 to one of the inventors of the present application discloses a sensor array for detecting biomarkers for cancer in breath samples. The sensor array is based on 2D films or 3D assemblies of conductive nanoparticles capped with an organic coating wherein the nanoparticles are characterized by a narrow size distribution.

WO 2008/124187 discloses a method for diagnosis or monitoring a disease or condition in an individual comprising: (a) collecting one or more biological sample from said individual, wherein the biological sample(s) contain proteins, lipids and nucleic acids of the individual; (b) analyzing the proteins and/or lipids from a biological sample to determine selective metabolites and oxidation products of arachidonic acid (AHA), docosahexanoic acid (DHA) and eicosapentaenoic acid (EPA); wherein said analyzing results in a metabolic determination of oxidative stress and lipids; and (c) analyzing the nucleic acids from a biological sample to determine the genotype and/or expression of genes involved in oxidative stress and/or lipid metabolism; wherein the existence or severity of a disease or condition is determined.

WO 2007/086986 discloses a method for detecting a target analyte/biomarker in exhaled breath comprising: a) exposing to the exhaled breath a molecular recognition agent capable of selectively binding to the target analyte/biomarker, wherein the molecular recognition agent is linked with a signaling agent; and b) detecting a signal generated by the signaling agent.

WO 2005/079669 discloses a method for diagnosing a predetermined condition in a subject including AD, said method comprising the steps of: (i) determining the amount, or relative amount, of a predetermined diagnostic species in a first breath sample; (ii) determining the amount, or relative amount, of said predetermined diagnostic species in a second breath sample; (iii) relating the results of steps (i) and (ii) with the presence or absence of said predetermined condition; wherein said first sample and second sample are ex vivo and are derived from different phases of a breathing cycle of said subject.

WO 2003/094932 discloses the use of carbon monoxide (CO) as a biomarker and therapeutic agent of conditions and disease states including, inter alia, AD.

WO 2000/061002 discloses a method for the assessment of psychiatric or neurological conditions, including AD, the method comprising determining the presence and/or amount of ethane or butane in the expired breath of the patient.

At present, no simple and reliable technique is available for early diagnosis of AD. There further remains an unmet need for the monitoring of AD progression using breath biomarkers thus affording adequate AD management.

SUMMARY OF THE INVENTION

The present invention provides a system and methods for diagnosing, monitoring, or prognosing Alzheimer's disease in a subject.

The system and method of the present invention provide improved sensitivity and selectivity for diagnosis, prognosis and monitoring Alzheimer's disease (AD), and differentiating between AD and Parkinson's disease patient populations. The present invention is based in part on the unexpected finding that a sensor array comprising at least one sensor comprising a random network of carbon nanotubes coated with cyclodextrin or cyclodextrin derivatives and/or at least one sensor comprising metal nanoparticles capped with various organic coatings provide enhanced sensitivity and selectivity for volatile biomarkers in breath samples which are indicative of Alzheimer's disease. The use of the sensor array in conjunction with a learning and pattern recognition algorithm provides the discrimination between Alzheimer's disease and Parkinson's disease patient populations thus offering significant advantages over the prior art. Hence, the present invention provides a fast and reliable diagnosis of AD allowing a comprehensive AD management, including monitoring of disease progression.

According to one aspect, the present invention provides a system for diagnosing, monitoring, or prognosing AD, the system comprising: (a) an apparatus comprising at least one sensor comprising nanomaterials selected from single walled carbon nanotubes coated with cyclodextrin or a derivative thereof and metal nanoparticles capped with an organic coating; (b) a detection means; and (c) a processing unit comprising a learning and pattern recognition analyzer wherein the learning and pattern recognition analyzer receives sensor output signals and compares them to stored data.

In one embodiment, the cyclodextrin or cyclodextrin derivative is selected from the group consisting of α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-6$^4$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono[6-(o-amino-phenyeimino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, heptakis(2,3,6-tri-O-methyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the present invention.

In another embodiment, the cyclodextrin or cyclodextrin derivative is selected from the group consisting of β-cyclodextrin, carboxy-methylated β-cyclodextrin, hydroxypropyl-β-cyclodextrin, heptakis(2,3,6-tri-O-methyl)-β-cyclodextrin and combinations thereof. Each possibility represents a separate embodiment of the present invention.

In yet another embodiment, the single walled carbon nanotubes are organized in a random network configuration.

In other embodiments, the single walled carbon nanotubes have diameters ranging from about 0.9 nanometer to about 5 nanometers, and lengths ranging from about 1 micrometer to about 50 micrometers.

In further embodiments, the metal nanoparticles are selected from the group consisting of Au, Ag, Ni, Co, Pt, Pd, Cu, and Al nanoparticles. Each possibility represents a separate embodiment of the present invention.

In some embodiments, the organic coating of the metal nanoparticles comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof. Each possibility represents a separate embodiment of the present invention.

In particular embodiments, the organic coating of the metal nanoparticles is selected from the group consisting of 3-mercapto-propionate and 2-mercapto-benzoazole. Each possibility represents a separate embodiment of the present invention.

In other embodiments, the metal nanoparticles have a morphology selected from a cubic, a spherical, and a spheroidal morphology. Each possibility represents a separate embodiment of the present invention.

In certain embodiments, the at least one sensor is configured in a form selected from the group consisting of a capacitive sensor, a resistive sensor, an impedance sensor, and a field effect transistor sensor. Each possibility represents a separate embodiment of the present invention.

In some embodiments, the system comprises a single sensor.

In other embodiments, the system comprises a plurality of sensors, for example between 2 and 6 sensors. In additional embodiments, the plurality of sensors comprises at least one sensor comprising single walled carbon nanotubes coated with cyclodextrin or a derivative thereof and at least one sensor comprising metal nanoparticles capped with an organic coating.

In other embodiments, the detection means comprises a device for measuring changes in resistance, conductance, alternating current (AC), frequency, capacitance, impedance, inductance, mobility, electrical potential, optical property or voltage threshold. Each possibility represents a separate embodiment of the present invention.

In further embodiments, the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor. Each possibility represents a separate embodiment of the present invention. In one embodiment, the at least one algorithm is discriminant function analysis (DFA).

In another aspect, the present invention provides a method of diagnosing, monitoring, or prognosing Alzheimer's disease in a subject, the method comprising the steps of: (a) providing a system as disclosed herein; (b) exposing the at least one sensor to a test exhaled breath sample; (c) measuring at least one response induced parameter from the at least one sensor upon exposure to the test sample to obtain a response pattern; and (d) analyzing the response pattern obtained in step (c) using a learning and pattern recognition algorithm by comparing it to stored data obtained from a control sample whereby a significantly different response pattern of the test sample as compared the control sample is indicative of AD.

In some embodiments, the method disclosed herein further provides the differentiation between healthy subjects, subjects having Alzheimer's disease, and subjects having Parkinson's disease (PD).

In another embodiment, the method of the present invention further comprises the step of concentrating the test exhaled breath sample prior to step (b) using at least one of a breath concentrator and a dehumidifying unit.

In certain embodiments, the response pattern is formed by the sensor detection of at least one volatile biomarker which is indicative of AD. In particular embodiments, the at least one volatile biomarker which is indicative of AD is selected from styrene, 1-methyl-2-(1-methylethyl)-benzene, 4-methyl-octane, 2,6,10-trimethyl-dodecane, 3,7-dimethyl-decane, butylated hydroxytoluene, 2,4-dimethyl-1-heptene, 2,3-dimethyl-heptane, propyl-benzene, 2,2,4,6,6-pentamethyl-heptane, 2,5,6-trimethyl-octane, 5-ethyl-2-methyl-octane, 2,6,10,14-tetramethyl-hexadecane, 3,7-dimethyl-propanoate-2,6-octadien-1-ol, 2,3,5-trimethyl-hexane, 1-methylethyl-benzene, 1-methylpropyl-cyclooctane, 2,2-dimethylpropanoic acid, 2-ethylhexyl tetradecyl ester oxalic acid, 2-butyl-1-octanol, dodecane, 1-chloro-nonadecane, 3-ethyl-2,2-dimethyl-pentane, and 1,1'-oxybis-octane. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a method of diagnosing, monitoring, or prognosing AD using at least one sensor comprising carbon nanotubes coated with cyclodextrin or derivatives thereof and/or at least one sensor comprising metal nanoparticles capped with an organic coating (e.g. mercapto derivatives). The invention further provides a method of distinguishing between healthy subjects, subjects having AD and subjects having PD.

The present invention provides a system which is suitable for the diagnosis, monitoring, or prognosis of AD. The system includes at least one chemically sensitive sensor as described herein, a detection means and a processing unit which utilizes a learning and pattern recognition algorithm to receive sensor output signals and compare them to stored data.

According to one embodiment, the at least one sensor comprises single-walled carbon nanotubes (SWCNTs) coated with cyclodextrin or cyclodextrin derivative wherein the nanotubes are arranged in a random network configuration. In some embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The substrate having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are now available from commercial sources.

Other CVD methods include the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotubes" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm) More preferably, the single-walled carbon nanotubes have diameters ranging from about 0.7 nm to about 50 nm and lengths ranging from about ranging from about 250 nm to about 1 mm. Even more preferably, the single-walled carbon nanotubes have diameters ranging from about 0.8 nm to about 10 nm and lengths ranging from about 0.5 micrometer (μm) to about 100 μm. Most preferably, the single-walled carbon nanotubes of the present invention have diameters ranging from about 0.9 nm to about 5 nm and lengths ranging from about 1 μm to about 50 μm.

According to the principles of the present invention, the single walled carbon nanotubes are coated with cyclodextrin or a cyclodextrin derivative. Suitable cyclodextrin or derivative thereof include, but are not limited to, α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-$6^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, heptakis(2,3,6-tri-O-methyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the present invention. Exemplary coatings of the single walled carbon nanotubes include β-cyclodextrin, carboxy-methylated β-cyclodextrin, hydroxypropyl-β-cyclodextrin, heptakis(2,3,6-tri-O-methyl)-β-cyclodextrin and combinations thereof. Each possibility represents a separate embodiment of the present invention.

According to some embodiments, the at least one sensor comprises nanoparticles comprising conductive metal cores which are capped with an organic coating. Suitable non-limiting examples of conductive metal cores include, but are not limited to, Au, Ag, Ni, Co, Pt, Pd, Cu, and Al nanoparticles. Each possibility represents a separate embodiment of the invention.

In one embodiment, the coating of the conductive nanoparticle cores comprises a monolayer or multilayers of organic compounds, wherein the organic compounds can be small molecules, monomers, oligomers or polymers. Each possibility represents a separate embodiment of the present invention. Suitable organic compounds include, but are not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkanethiolates, arenethiolates, (γ-mercaptopropyl)tri-methyloxysilane, dialkyl disulfides and combinations thereof. Each possibility represents a separate embodiment of the present invention. In particular embodiments, the organic coating of the metal nanoparticles comprises 3-mercapto-propionate. In other embodiments, the organic coating of the metal nanoparticles comprises 2-mercapto-benzoazole.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In a currently preferred embodiment, the alkyl group has 3-24 carbons designated here as $C_3$-$C_{24}$ alkyl. The alkyl group may be unsubstituted or substituted by one or more groups selected from alcohol, ketone, aldehyde, halogen, carbonate, carboxylate, carboxylic acid, acyl, amido, amide, amine, imine, ester, ether, cyano, nitro, and azido. Each possibility represents a separate embodiment of the present invention.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halogen, haloalkyl, ($C_1$-$C_8$)alkyl, ($C_2$-$C_8$)alkenyl, ($C_2$-$C_8$)alkynyl, ($C_6$-$C_{10}$)aryl, alcohol, ketone, aldehyde, carbonate, carboxylate, carboxylic acid, acyl, amido, amide, amine, imine, ester, ether, cyano, nitro, azido, and the like. Each possibility represents a separate embodiment of the present invention.

Sensors comprising metal nanoparticles capped with various organic coatings can be synthesized as is known in the art, for example using the two-phase method (Brust et al., J. Chem. Soc. Chem. Commun., 1994, 801, 2) with some modifications (Hostetler et al., Langmuir, 1998, 14, 24). Capped gold nanoparticles can be synthesized by transferring $AuCl_4^-$ from aqueous $HAuCl_4.xH_2O$ solution to a toluene solution by the phase-transfer reagent TOAB. After isolating the organic phase, excess thiols are added to the solution. The mole ratio of thiol:$HAuCl_4.xH_2O$ can vary between 1:1 and 10:1, depending on the thiol used. This is performed in order to prepare mono-disperse solution of gold nanoparticles in average size of about 3.5-5 nm. Exemplary procedures include, but are not limited to, thiol:Au mole ratios of 10:1 and 1:1 for dodecanethiol and butanethiol-capped gold nanoparticles, respectively at an average size of 5 nm. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with 2-mercaptobenzoazole can be synthesized by ligand-exchange method from pre-prepared hexanethiol-capped gold nanoparticles. In a typical reaction, excess of thiol, 2-mercaptobenzoazole, is added to a solution of hexanethiol-capped gold nanoparticles in toluene. The solution is kept under constant stirring for few days in order to allow as much ligand conversion as possible. The nanoparticles are purified from free thiol ligands by repeated extractions. The metal nanoparticles may have any desirable morphology including, but not limited to, a cubic, a spherical, and a spheroidal morphology. Each possibility represents a separate embodiment of the invention.

The synthesized nanoparticles can then be assembled (e.g. by a self-assembly process) to produce a film of capped nanoparticles. The term "film", as used herein, corresponds to a configuration of well-arranged assembly of capped nanoparticles. 2D or 3D films of capped nanoparticles may also be used. Exemplary methods for obtaining well-ordered two or three dimensional assemblies of capped nanoparticles include, but are not limited to, i. Random deposition from solution of capped nanoparticles on solid surfaces. The deposition is performed by drop casting, spin coating, spray coating and other similar techniques.

ii. Field—enhanced or molecular-interaction-induced deposition from solution of capped nanoparticles on solid surfaces.

iii. Langmuir-Blodgett or Langmuir-Schaefer techniques. The substrate is vertically plunged through self-organized/well-ordered 2D monolayer of capped nanoparticles at the air-subphase interface, wherein the latter is being subsequently transferred onto it. Multiple plunging of the substrate through the 2D monolayer of capped nanoparticles at the air-subphase interface, results in the fabrication of the 3D-ordered multilayers of capped nanoparticles.

iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating capped nanoparticles from nanometer-scale to a mesoscopic scale (Zhao et al., J. Mater. Chem., 1997, 7(7), 1069).

v. Various combinations of Langmuir-Blodgett or Langmuir-Schaefer methods with soft lithographic techniques can be used to produce patterned Langmuir-Blodgett films of molecularly modified capped nanoparticles which are transferred onto solid substrates.

vi. Printing on solid-state or flexible substrates using an inject printer designated for printed electronics. A solution containing the capped nanoparticles is used as a filling material (or "ink") of the printing head according to procedures well known in the art.

The sensors of the present invention can be configured as any one of the various types of electronic devices, including, but not limited to, capacitive sensors, resistive sensors, impedance sensors, field effect transistor sensors, and the like, or combinations thereof. Each possibility represents a separate embodiment of the present invention.

In one embodiment, the system of the present invention comprises a single sensor. In alternative embodiments, the system of the present invention comprises a plurality of sensors (sensor array), for example between 2 and 6 sensors. In some embodiments, the sensor array comprises a sensor of single walled carbon nanotubes coated with cyclodextrin or a derivative thereof and/or a sensor of metal nanoparticles capped with an organic coating. In other embodiments, the sensor array comprises the combination of a sensor of single walled carbon nanotubes coated with cyclodextrin or a derivative thereof and a sensor of metal nanoparticles capped with an organic coating. In one embodiment, the sensor array comprises one sensor of carbon nanotubes coated with β-cyclodextrin, one sensor of carbon nanotubes coated with hydroxypropyl-β-cyclodextrin, and one sensor of spherical gold nanoparticles coated with 3-mercapto-propionate. In another embodiment, the sensor array comprises one sensor of carbon nanotubes coated with β-cyclodextrin, one sensor of carbon nanotubes coated with carboxy-methylated β-cyclodextrin, one sensor of carbon nanotubes coated with hydroxypropyl-β-cyclodextrin, one sensor of carbon nanotubes coated with heptakis(2,3,6-tri-O-methyl)-β-cyclodextrin, one sensor of spherical gold nanoparticles coated with 2-mercapto-benzoazole, and one sensor of spherical gold nanoparticles coated with 3-mercapto-propionate.

In certain embodiments, the sensors comprise one or more conducting elements. The conducting elements may include a source and a drain electrode separated from one another by a source-drain gap.

The system disclosed herein may further comprise a gate electrode wherein the sensor signal may be indicative of a certain property of the nanomaterial under the influence of a gate voltage. Alternatively, the sensor signal may be indicative of a capacitance property of the nanomaterial.

The sensor signal may be induced, according to the principles of the present invention by a change in any one or more of conductivity, resistance, impedance, capacitance, inductance, or optical properties of the sensor upon exposure to volatile biomarkers. Each possibility represents a separate embodiment of the present invention. Changes in the optical properties of the sensor network can be measured using e.g., spectroscopic ellipsometry.

The sensor signal is detected by a detection means. Suitable detection means include devices which are susceptible to a change in any one or more of resistance, conductance, alternating current (AC), frequency, capacitance, impedance, inductance, mobility, electrical potential, an optical property and voltage threshold. Each possibility represents a separate embodiment of the present invention. In additional embodiments, the detection means includes devices which are susceptible to swelling or aggregation of nanomaterials as well as devices which are susceptible to a change in any one or more of optical signal, florescence, chemiluminsence, photophorescence, bending, surface acoustic wave, piezoelectricity and the like. Each possibility represents a separate embodiment of the present invention.

According to another embodiment, the present invention further provides a processing unit comprising a learning and pattern recognition analyzer, wherein the learning and pattern recognition analyzer receives sensor output signals and analyses them by various pattern analysis algorithms to produce an output signature. By comparing an unknown signature with a database of stored or known signatures, volatile biomarkers can be identified. The analyzer utilizes learning and pattern recognition algorithms comprising artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention. In an exemplary embodiment, the algorithm used for processing the data is discriminant function analysis (DFA).

Additional algorithms suitable for identifying patterns of volatile biomarkers and quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms Each possibility represents a separate embodiment of the present invention. In some embodiments, the Fisher linear discriminant analysis (FLDA) and canonical discriminant analysis (CDA) and combinations thereof are used to compare the output signature and the available data from the database. After analysis is completed, the resulting information can be displayed on a display or transmitted to a host computer.

The present invention further provides a method of diagnosing, monitoring, or prognosing AD in a subject using the system of the present invention. The at least one sensor is exposed to a test exhaled breath sample and at least one response induced parameter is measured by a detection means. The obtained signal is a response pattern which is preferably analyzed using a learning and pattern recognition algorithm by comparing it to stored data obtained from a control sample whereby a significantly different response pattern of the test sample as compared the control sample is indicative of AD.

The term "significantly different" as used herein refers to a statistically significant quantitative difference between the pattern of the test sample and the pattern of a control sample. A statistically significant difference can be determined by any test known to the person skilled in the art. Common tests for statistical significance include, among others, t-test, ANOVA1 Kruskal-Wallis, Wilcoxon, Mann-Whitney and odds ration. Individual samples (of unknown status) can be compared with negative control samples obtained from subjects who are not afflicted with AD. A statistically significant elevation or reduction in the particular response parameter being measured between the test and control sample qualifies as significant difference. A set of control samples can be stored as a reference collection for multiple analyses. In additional embodiments, the unknown test sample may be compared to a sample obtained from a subject known to be afflicted with PD. In accordance with these embodiments, the present invention encompasses the discrimination between populations of healthy subjects, subjects having AD and subjects having PD.

The method of the present invention may further comprise the step of concentrating the test exhaled breath sample prior to the measurement using a breath concentrator and/or a dehumidifying unit.

Breath pre-concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., Anal. Bioanal. Chem., 2006, 386, 1059-1073; Coelho et al., J. Chromatography B, 2007, 853, 1-9).

II. Sorbent Tubes—Sorbent tubes are typically composed of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than −160° C.) condensation process.

A dehumidifier that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the larger the amount of water that is adsorbed before equilibrium is reached. Silica gel is advantageous as a drying substance since the process of drying requires no chemical reaction and it produces no by products or side effects.

III. Activated carbon—is formed by processing charcoal to an extremely porous carbon substance. Due to its high degree of microporosity, the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

The method of the present invention enables the detection of a single volatile biomarker as well as the detection of a plurality of volatile biomarkers and the unique pattern of these biomarkers which characterizes AD. In certain embodiments, the volatile biomarkers which are indicative of AD include, but are not limited to, at least one of styrene, 1-methyl-2-(1-methylethyl)-benzene, 4-methyl-octane, 2,6,10-trimethyl-dodecane, 3,7-dimethyl-decane, butylated hydroxytoluene, 2,4-dimethyl-1-heptene, 2,3-dimethyl-heptane, propyl-benzene, 2,2,4,6,6-pentamethyl-heptane, 2,5,6-trimethyl-octane, 5-ethyl-2-methyl-octane, 2,6,10,14-tetramethyl-hexadecane, 3,7-dimethyl-propanoate-2,6-octadien-1-ol, 2,3,5-trimethyl-hexane, 1-methylethyl-benzene, 1-methylpropyl-cyclooctane, 2,2-dimethylpropanoic acid, 2-ethylhexyl tetradecyl ester oxalic acid, 2-butyl-1-octanol, dodecane, 1-chloro-nonadecane, 3-ethyl-2,2-dimethyl-pentane, and 1,1'-oxybis-octane. Each possibility represents a separate embodiment of the present invention.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Test Population

The test population included 57 non-smoking volunteers (15 AD patients, 30 PD patients and 12 healthy controls) at the age of 37-85. The AD patients were recruited from the out-patient population of the Cognitive Unit, Rambam Health Care Campus (Haifa, Israel). The control group of PD patients (Hoehn and Yahr stages 1-4; Goetz et al., Mov. Disord., 2004, 19, 1020-1028; Hoehn et al., Neurology, 1967, 17, 427-442) was recruited from out-patients of the Department of Neurology and the Cognitive Unit of the Rambam Health Care Campus and the healthy controls were recruited from the patients' accompanying persons. The AD and PD patients were diagnosed through assessment of clinical symptoms in the aforementioned specialist clinics and the healthy controls were declared healthy (not afflicted with AD or PD) in the same specialist setting. All AD patients were medicated, but medication varied between patients. A summary of the patient characteristics is provided in Table 1.

TABLE 1

Summary of the clinical characteristics of 57 non-smoking volunteers that were tested in this study

| | No. of tested subjects | Average age ± STD | Male:Female ratio |
|---|---|---|---|
| AD patients | 15 | 68 ± 10 | 7:8 |
| Control group I: Healthy subjects | 12 | 61 ± 7 | 5:7 |
| Control group II: PD patients (HY[(1)] stages 1-4) | 30 | 62 ± 10 | 17:13 |

[(1)]HY = Hoehn and Yahr

Ethical approval was obtained from the Rambam Healthcare Campus and Technion's committee for supervision of human experiments, Haifa, Israel. The volunteers or their legal guardians gave their written informed consent prior to the breath collection, and all experiments were performed according to the guidelines of the Rambam Healthcare Campus and Technion's committee for supervision of human experiments.

Example 2

Clinical Study

The clinical study was cross-sectional. Highly accurate diagnosis was achieved through clinical examination in a specialist clinic and served as reference standard. The tested AD patients were compared with two test groups, healthy controls and PD patients. Patterns of volatile biomarkers for the three test groups were obtained by comparing (i) AD patients and healthy controls, (ii) AD patients and PD patients, and (iii) all three test groups together. All subjects who were included in this study were non-smokers. One male AD patient was excluded after recruitment because of his long-time heavy smoking habits. The three test groups were approximately age matched. The gender ratio of the AD patients was similar to that of healthy controls but was different form that of the PD control group. This relaxation of the recruiting criteria is acceptable, since the sensors that were used to detect volatile biomarkers' patterns have been specially tailored to show little sensitivity to confounding factors such as gender (cf. Peng et al., Br. J. Cancer, 2010, 103, 542-551).

Example 3

Breath Collection

Exhaled alveolar breath was collected in a controlled manner from AD patients and from control subjects in the hospital environment. The inhaled air was cleared of ambient contaminants by repeatedly inhaling to total lung capacity for 3-5 minutes through a mouthpiece (purchased from Eco Medics, Duerten, Switzerland) that contained a filter cartridge on the inspiratory port, thus greatly reducing the concentration of exogenous volatile organic compounds and removing 99.99% of the exogenous compounds from the air during inspiration. Since some typical hospital contaminations might be present in very large concentrations (Amann et al., Euro. Resp. Soc. Monograph, 2010, 49, 96-114), the unfiltered hospital air was also sampled. GC-MS in conjugation with Solid-Phase Micro-Extraction (SPME) found the following typical hospital contaminants: 2-methyl-2-propanol, ethanol and methyl-isobutyl-ketone. Trace amounts of these compounds were identified in less than 23% of the study population, indicating that the air filtration was efficient. Immediately after lung washout, subjects exhaled through a separate exhalation port of the mouthpiece against 10-15 cm $H_2O$ pressure to ensure closure of the vellum so that nasal entrainment of gas was excluded. Exhaled breath is composed of a mixture of alveolar air and respiratory dead space air. The dead space was automatically filled into a separate bag and the alveolar breath into a 750 ml Mylar sampling bag (purchased from Eco Medics). The described breath collection was performed in a single-step process that did not require the subject to change the dead space and alveolar breath bags. The Mylar bags were re-used and thoroughly cleaned before each use with flowing $N_2$ (99.999% purity) gas for 5-8 min. Notably, GC-MS in conjugation with Solid-Phase Micro-Extraction (SPME) has shown that this purification process eliminates 98% of contaminants and/or volatile biomarkers from the previous sample tested in a specific Mylar bag. Between one and two bags were collected per test subject for analysis with GC-MS and/or for analysis with the sensors. All bags were analyzed within 7 days from the time of breath collection, much before the allowed 3-weeks storage period, after which, according to the control experiments, the samples might start to deteriorate (Peng et al., Nature Nanotech., 2009, 4, 669; Peng et al., Br. J. Cancer, 2010, 103, 542; Peng et al., Nano Lett., 2008, 8, 3631).

Example 4

Breath Analysis Using the Sensors

The breath samples were tested using a sensor array in accordance with the present invention. The array was composed of either three or six sensors that were based on different organically functionalized nanomaterials. The nanomaterials used for these experiments contained (i) random networks of single-walled carbon nanotubes (RN-CNTs) that were functionalized with a layer of β-cyclodextrin (CD) or its derivatives, and (ii) gold (Au) spherical nanoparticles coated with different mercapto derivatives as specified in Table 2. The sensor fabrication was performed as described in details in Peng at al., Nano Lett., 2008, 8, 3631-3635; Dovgolevsky et al., Small, 2008, 4, 2059-2066; and Haick et al., ACS Nano, 2009, 3, 1258-1266, the contents of each of these references are hereby incorporated in their entirety. Each sensor showed a characteristic response to all (or to a certain subset) of the volatile biomarkers found in the exhaled breath samples.

TABLE 2

Nanomaterials and organic functionalities of the sensors

| Sensor No. | Nano-material | Organic functionality | AD and healthy control | AD and PD | AD healthy and PD |
|---|---|---|---|---|---|
| 1 | CNTs | β-CD | x | x | x |
| 2 | | Carboxy-methylated β-CD | | | x |
| 3 | | hydroxypropyl-β-CD | x | x | x |
| 4 | | Heptakis(2,3,6-tri-O-methyl)-β-CD | | | x |
| 5 | Gold | 2-Mercapto-benzoazole | | | x |
| 6 | nanoparticles | 3-Mercapto-propionate | x | x | x |

CNT: carbon nanotubes;
CD = cyclodextrin

Example 5

Breath Analysis Using GC-MS

The constituent volatile biomarkers of the collected breath were identified using GC-MS (GC-6890N; MS-5975; Agilent Technologies Ltd). The GC-MS analysis was preceded by SPME for pre-concentrating the volatile biomarkers in the breath samples as follows: A manual SPME holder with an extraction fiber was inserted into the Mylar bag for 30 minutes before being delivered to the GC-MS. Fibers with polydimethylsiloxane-divinylbenzene coating were obtained from Sigma-Aldrich. The extracted fiber in the manual SPME holder was inserted into the injector of the GC (splitless mode). The following oven profile was used: 10 min at 35° C., 7.5° C. per min to 130° C., 13° C. per min to 290° C., 1 min at 290° C. A capillary column SLB-5MS low phenyl methyl siloxane content (30 m length, 0.25 mm internal diameter, 0.50 µm thickness, from Sigma-Aldrich) was used. The column pressure was set at 8.22 PSI, and the initial flow rate was 1.0 ml per min. Identities of the volatile biomarkers were determined by a spectral library match using the retention time. The volatile biomarkers common for >75% of the healthy and/or PD, and/or AD samples, as well as their abundance with experimental error (standard error, SE), were identified using the Automated Mass Spectral Deconvolution and Identification System (AMDIS) software.

Example 6

Statistical Analysis

The signals from the senor array were analyzed using discriminant factor analysis (DFA) as described in Ionescu et al., Analyst, 2002, 127, 1237-1246 and Brereton, Application of Mathematics Statistics to Laboratory Systems, Chichester, Ellis Horwood, 1990. In particular, DFA is a linear, supervised pattern recognition method. The classes to be discriminated are defined before the analysis is performed. DFA determines the linear combinations of the sensor values such that the variance within each class is minimized and the variance between classes is maximized. The DFA output variables (viz. canonical variables) are obtained in mutually orthogonal dimensions. The first canonical variable will be the most powerful discriminating dimension, but the following canonical variables might also represent additional dimensions of differentiation. Thus, DFA effectively reduces the multidimensional experimental data, improves the human perception of the data and allows the distinction of clusters through visual perception of the first or the first and second canonical variables.

Four features (response induced parameters) were read out per sensor that relate to the normalized resistance change after exposure to the breath samples in the middle and at the end of the signal. The classification success rate of the binary problems was estimated through leave-one-out cross validation. For this purpose, DFA was computed using a training data set that excluded one test sample. After the DFA computation, the test sample was projected onto the two-dimensional DFA space, defined by the first two canonical variables (CV1 and CV2) that were calculated using the training set. Thereby, the test sample was "blinded" against the DFA model so that its class affiliation was unknown. All possibilities of leaving out one sample were tested and the left out sample was classified as true positive (TP), true negative (TN), false positive (FP) and false negative (FN), using standard cluster analysis.

Figure 1A:
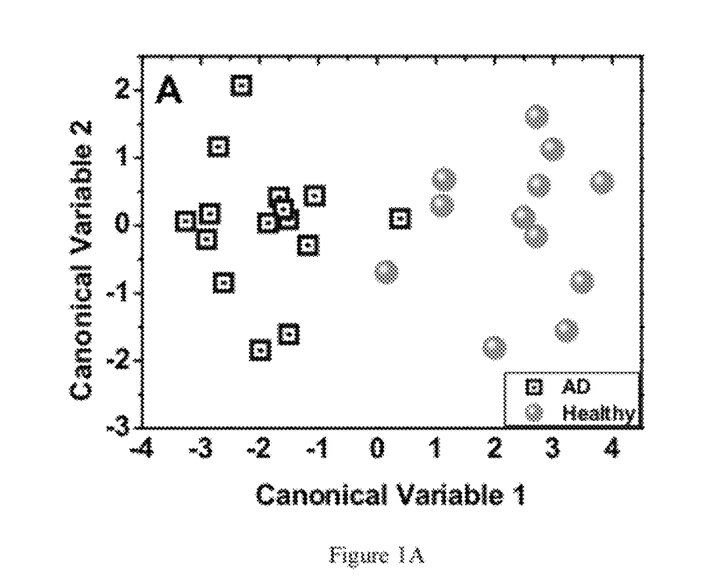
FIGS. 1A-1C. DFA plots of the first two canonical variables that were calculated from the responses of (1A) three sensors to breath samples of AD patient population (□) and healthy controls (※), (1B) the same three sensors to breath samples of AD (□) and PD (◇) patient populations, and (1C) an extended array of six sensors to breath samples of AD (□) and PD (◇) patients and healthy controls (※). Each patient is represented by 1 point in the plot.

Results:

The breath samples of 15 AD patients, 12 healthy controls and 30 PD patients were analyzed using the sensor array as described in Example 4. Two of the sensors were based on random network of single walled CNTs functionalized with β-cyclodextrin (β-CD) or β-CD derivative, and one sensor was based on organically functionalized spherical Au nanoparticles. In addition, the analysis was performed using each of these sensors alone. The AD states could clearly be depicted from both the healthy states and the PD states. During the statistical analysis of the sensor signals, the number of DFA input parameters was kept low enough to avoid overfitting. FIG. 1A shows that two distinct clusters, corresponding to AD and healthy states, can be observed in CV space. Indeed, the AD patients are distinguished from the healthy controls along the axis of the first canonical variable, with negative values for the former and positive values for the latter. The classification success rate was estimated through leave-one-out cross validation as described in Example 6 and the results are summarized in Table 3A. The sensitivity, specificity and accuracy of the classification were determined as 93%, 75% and 85%, respectively. When using each of these sensors alone, the sensitivity, specificity and accuracy of the classification were determined as 57% and 48%, and 53%, respectively.

Figure 1B:
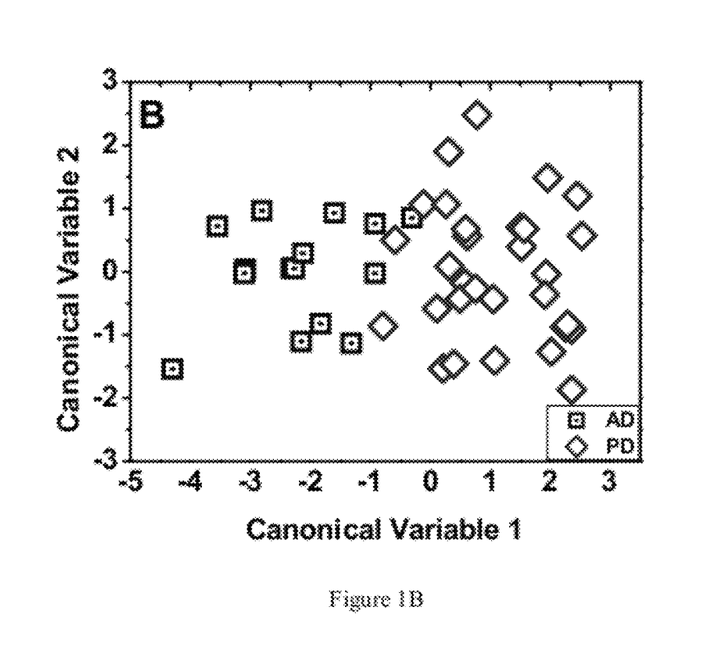
Figure 1C:
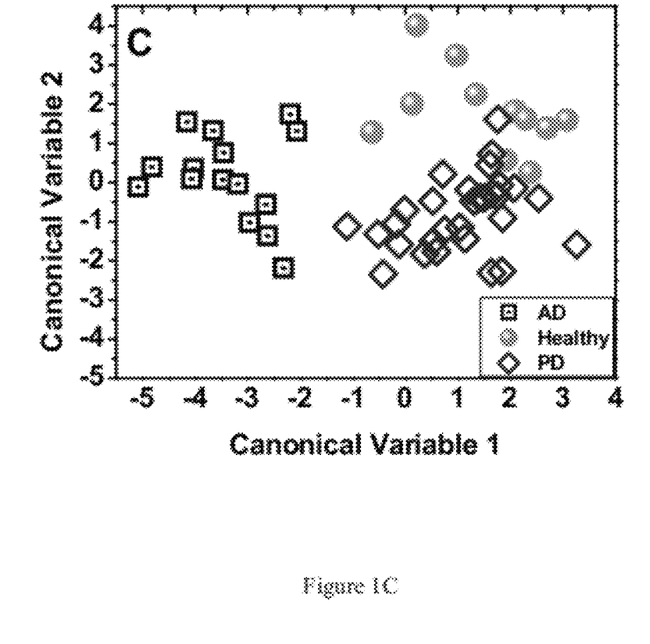

In order to provide the diagnosis and prognosis of AD suitable for clinical use, the diagnosis of AD should be distinguishable from the diagnosis of other neurodegenerative diseases such as PD, since patients of AD often suffer from clinical symptoms that are similar to those of PD patients. This may sometimes lead to the false diagnosis of either one of these diseases. FIG. 1B shows that very good separation of AD and PD patients could be achieved along the first canonical variable. The classification success rate was estimated through leave-one-out cross validation as described in Example 6 and the results are summarized in Table 3B. The sensitivity, specificity and accuracy of the classification of AD versus the PD control group were determined as 80%, 87% and 84%, respectively. Thus, the sensors of the present invention provide the diagnosis of AD with excellent sensitivity and specificity to afford the distinction of AD patients from healthy controls and from PD patients. FIG. 1C shows that all three test groups (AD, PD and healthy) could be distinguished in the same DFA plot, using an extended sensor array that contained six nano-sensors (Table 2). Noteworthy that the second canonical variable represents a considerable dimension of differentiation and that a larger overlap is observed between the two control groups. The use of more input parameters is permissible, because of the increased total number of samples. The clusters in FIGS. 1A, 1B and 1C appear differently in canonical variable space, because the DFA input data is different.

TABLE 3A&3B

Classification success, estimated using the leave-one-out cross validation (A)

|  | Classified as AD | Classified as healthy |
|---|---|---|
| AD | 14 | 1 |
| healthy | 3 | 9 |

(B)

|  | Classified as AD | Classified as PD |
|---|---|---|
| AD | 12 | 3 |
| PD | 4 | 26 |

The chemical composition of the exhaled breath of AD patients was analyzed and compared to the breath of healthy controls in order to glean information regarding the biomarkers which form the patterns that are detected by the sensors of the present invention. A representative sub-set of the collected breath samples were analyzed using GC-MS in combination with SMPE as described in Example 5. Certain differences in the average chemical composition of the breath samples from AD patients vs. healthy controls were found to exist. Twenty-four substances that differ in average abundance in breath samples taken from the AD patients as compared to healthy controls are thus considered as potential volatile biomarkers which are indicative of AD.

Figure 2:
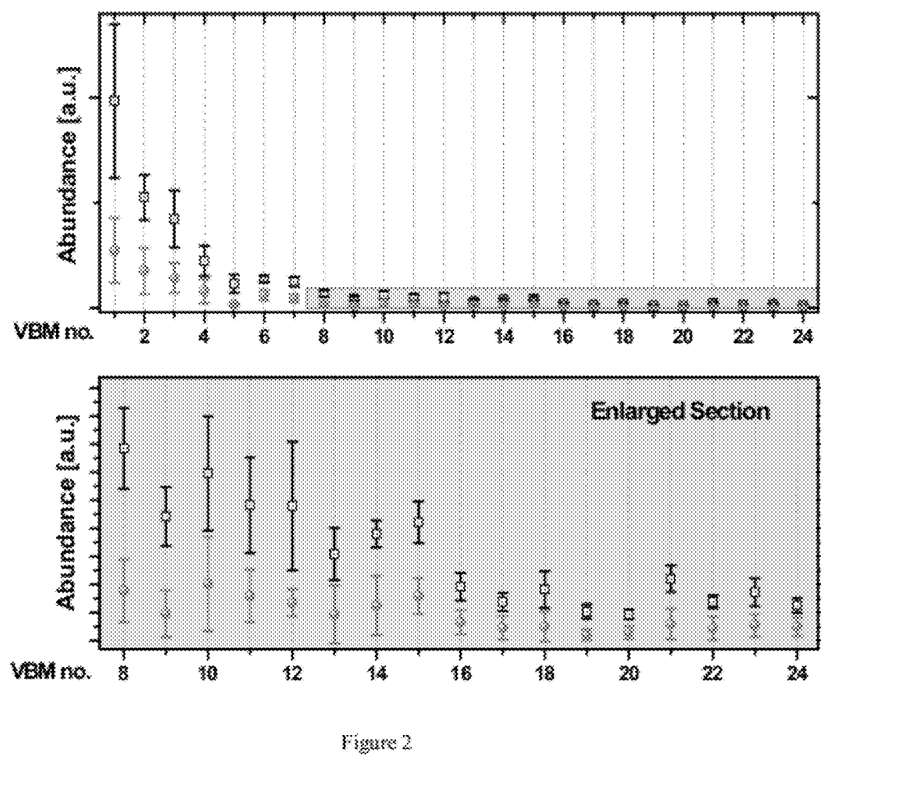
FIG. 2. Abundance of 24 volatile biomarkers (VBMs) that were found in the breath of >80% of both AD patients (□) and healthy controls (※). The symbols represent the average abundance and the error bars mark the borders of the 95% CIs. The VBMs are listed in Table 4.

FIG. 2 shows the volatile biomarkers that (i) were present in >80% of the AD patients and >80% of the healthy controls and (ii) that showed no (or little) overlap in average abundance (95% confidence interval, CI=1.96×SE). An identification of the detected compounds through spectral library match and retention times was performed (Table 4). The comparison between patients was based on compound masses and retention times. Without being bound by any theory or mechanism of action, most compounds can be linked to oxidative stress (e.g. styrene), which is known to play a major role in the development and progression of AD. Noteworthy, the substances identified in the unfiltered hospital air as typical hospital contaminants (2-methyl-2-propanol, ethanol and methyl-isobutyl-ketone) were found in less than 10% of the tested subjects.

TABLE 4

Identification of the compounds that were found in >80% of the healthy and AD test groups and are elevated in the AD patient group (see FIG. 2)

| VBM No. | Compound name | Main target mass [m/z] | Retention time |
|---|---|---|---|
| 1 | Styrene | 104 | 16.6 |
| 2 | Benzene, 1-methyl-2-(1-methylethyl)- | 119 | 21.0 |
| 3 | Octane, 4-methyl- | 43 | 14.1 |
| 4 | Dodecane, 2,6,10-trimethyl- | 57 | 20.5 |
| 5 | Decane, 3,7-dimethyl- | 43 | 22.6 |
| 6 | Butylated hydroxytoluene | 205 | 35.8 |
| 7 | 2,4-Dimethyl-1-heptene | 43 | 13.5 |
| 8 | Heptane, 2,3-dimethyl- | 43 | 13.9 |
| 9 | Benzene, propyl- | 91 | 18.6 |
| 10 | Heptane, 2,2,4,6,6-pentamethyl- | 57 | 20.2 |
| 11 | Octane, 2,5,6-trimethyl- | 57 | 17.8 |
| 12 | Octane, 5-ethyl-2-methyl- | 43 | 22.8 |
| 13 | Hexadecane, 2,6,10,14-tetramethyl- | 57 | 26.3 |
| 14 | 2,6-Octadien-1-ol, 3,7-dimethyl-, propanoate, (E)- | 57 | 20.8 |
| 15 | Hexane, 2,3,5-trimethyl- | 43 | 12.3 |
| 16 | Benzene, (1-methylethyl)- | 105 | 17.4 |
| 17 | Cyclooctane, (1-methylpropyl)- | 69 | 32.2 |
| 18 | 2,2-Dimethylpropanoic acid | 69 | 31.8 |
| 19 | Oxalic acid, 2-ethylhexyl tetradecyl ester | 57 | 32.4 |
| 20 | 1-Octanol, 2-butyl- | 57 | 28.6 |
| 21 | Dodecane | 57 | 25.7 |
| 22 | Nonadecane, 1-chloro- | 57 | 24.8 |
| 23 | Pentane, 3-ethyl-2,2-dimethyl- | 57 | 18.3 |
| 24 | Octane, 1,1'-oxybis- | 57 | 33.7 |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of distinguishing Alzheimer's disease from Parkinson's disease and neither Alzheimer's disease nor Parkinson's disease in a subject, the method comprising the steps of:
   (a) providing a system comprising an apparatus comprising at least two sensors, a first of said sensors comprising nanomaterials selected from the group consisting of single walled carbon nanotubes (SWCNTs) coated with β-cyclodextrin SWCNTs coated with carboxy-methylated β-cyclodextrin, SWCNTs coated with hydroxypropyl-β-cyclodextrin, and SWCNTs coated with heptakis(2,3,6-tri-O-methyl)-β-cyclodextrin, and a second of said sensors comprising nanomaterials selected from the group consisting of Au nanoparticles capped with 3-mercapto-propionate, and Au nanoparticles capped with 2-mercapto-benzoazole; and a processing unit comprising a learning and pattern recognition analyzer;
   (b) exposing the at least two sensors to a test exhaled breath sample;
   (c) measuring at least one response induced parameter from each of the at least two sensors upon exposure to the test sample to obtain a response pattern, wherein the response pattern is formed by the sensor detection of at least one volatile biomarker which is indicative of Alzheimer's disease;
   (d) analyzing the response pattern obtained in step (c) using the learning and pattern recognition analyzer by comparing the response pattern stored data obtained from a control sample and a Parkinson's disease sample, whereby a significantly different response pattern of the test sample as compared to the control sample and the Parkinson's disease sample is indicative of Alzheimer's disease, and
   (e) presenting the resulting information on a display or transmitting said information to a host computer using the processing unit.

2. The method of claim 1, for differentiating between healthy subjects, subjects having Alzheimer's disease and subjects having Parkinson's disease.

3. The method of claim 1, further comprising the step of concentrating the test exhaled breath sample prior to step (b) using at least one of a breath concentrator and a dehumidifying unit.

4. The method of claim 1, wherein the at least one volatile biomarker which is indicative of Alzheimer's disease is selected from the group consisting of styrene, 1-methyl-2-(1-methylethyl)-benzene, 4-methyl-octane, 2,6,10-trimethyl-dodecane, 3,7-dimethyl-decane, butylated hydroxytoluene, 2,4-dimethyl-1-heptene, 2,3-dimethyl-heptane, propyl-benzene, 2,2,4,6,6-pentamethyl-heptane, 2,5,6 trimethyl octane, 5-ethyl-2-methyl-octane, 2,6,10,14-tetramethyl-hexadecane, 3,7-dimethyl-propanoate-2,6-octadien-1-ol, 2,3,5-trimethyl-hexane, 1-methylethyl-benzene, 1-methylpropyl-cycooctane, 2,2-dimethylpropanoic acid, 2-ethylhexyl tetradecyl ester oxalic acid, 2-butyl-1-octanol, dodecane, 1-chloro-nonadecane, 3-ethyl-2,2-dimethyl-pentane, and 1,1'-oxybis-octane.

5. The method of claim 1, wherein the apparatus further comprises a sensor comprising SWCNTs coated with cyclodextrin, selected from the group consisting of α-cyclodextrin, γ-cyclodextrin, methyl-β-cyclodextrin, 2,6-dibutyl-β-cyclodextrin, 2,6-di-O-methyl-β-cyclodextrin, permethylated α-cyclodextrin-6$^4$-mono alcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated β-cyclodextrin, mono(6-cyclohexylamino-6-deoxy)-β-cyclodextrin, mono-(6-benzylimino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin and combinations thereof.

6. The method of claim 1, wherein the single walled carbon nanotubes are organized in a random network configuration.

7. The method of claim 1, wherein the apparatus further comprises a sensor comprising metal nanoparticles capped with an organic coating, wherein the metal nanoparticles are selected from the group consisting of Au, Ag, Ni, Co, Pt, Pd, Cu, and Al nanoparticles.

8. The method of claim 7, wherein the organic coating of the metal nanoparticles comprises compounds selected from the group consisting of alkylthiols, arylthiols, alkylarylthiols, alkylthiolates, w-functionalized alkanethiolates, arenethiolates, (γ-mercaptopropyl)tri-methyloxysilane, dialkyl disulfides and combinations thereof.

9. The method of claim 1, wherein the Au nanoparticles have a morphology selected from a cubic, a spherical, and a spheroidal morphology.

10. The method of claim 1, wherein the at least one sensor is configured in a form selected from the group consisting of a capacitive sensor, a resistive sensor, an impedance sensor, and a field effect transistor sensor.

11. The method of claim 1 comprising a single sensor.

12. The method of claim 1 comprising a plurality of sensors.

13. The method of claim 12 comprising between 2 and 6 sensors.

14. The method of claim 1, wherein the system further comprises a device that measures changes in at least one property of the at least one sensor, wherein the detection device is selected from the group consisting of a resistance measurement device, a conductance measurement device, an alternating current (AC) measurement device, a frequency measurement device, a capacitance measurement device, an impedance measurement device, an inductance measurement device, a mobility measurement device, an electrical potential measurement device, an optical property measurement device, a voltage threshold measurement device, a fluorescence measurement device, a chemiluminescence measurement device, a phosphorescence measurement device, a bending measurement device, a surface acoustic wave measurement device, and a piezoelectricity measurement device.

15. The method of claim 1, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

16. The method of claim 15, wherein the at least one algorithm is discriminant function analysis (DFA).

17. The method of claim 1, wherein the at least one sensor comprises Au nanoparticles capped with 3-mercapto-propionate.

18. A method of diagnosing, monitoring, or prognosing Alzheimer's disease in a subject, the method comprising the steps of:

(a) providing a system comprising an apparatus comprising at least one sensor comprising nanomaterials selected from the group consisting of single walled carbon nanotubes (SWCNTs) coated with β-cyclodextrin, SWCNTs coated with carboxy-methylated β-cyclodextrin, SWCNTs coated with hydroxypropyl-β-cyclodextrin, SWCNTs coated with heptakis(2,3,6-tri-O-methyl)-β-cyclodextrin, Au nanoparticles capped with 3-mercapto-propionate, and Au nanoparticles capped with 2-mercapto-benzoazole; and a processing unit comprising a learning and pattern recognition analyzer;

(b) exposing the at least one sensor to a test exhaled breath sample;

(c) measuring at least one response induced parameter from the at least one sensor upon exposure to the test sample to obtain a response pattern, wherein the response pattern is formed by the sensor detection of at least one volatile biomarker which is indicative of Alzheimer's disease, selected from the group consisting of 1-methyl-2-(1-methylethyl)-benzene, 4-methyl-octane, 2,6,10-trimethyl-dodecane, 3,7-dimethyl-decane, butylated hydroxytoluene, 2,4-dimethyl-1-heptene, 2,3-dimethyl-heptane, propyl-benzene, 2,2,4,6,6-pentamethyl-heptane, 2,5,6-trimethyl-octane, 5-ethyl-2-methyl-octane, 2,6,10,14-tetramethyl-hexadecane, 3,7-dimethyl-propanoate-2,6-octadien-1-ol, 2,3,5-trimethyl-hexane, 1-methylethyl-benzene, 1-methylpropyl-cyclooctane, 2,2-dimethylpropanoic acid, 2-ethylhexyl tetradecyl ester oxalic acid, 2-butyl-1-octanol, dodecane, 1-chloro-nonadecane, 3-ethyl-2,2-dimethyl-pentane, and 1,1'-oxybis-octane;

(d) analyzing the response pattern obtained in step (c) using the learning and pattern recognition analyzer by comparing the response pattern stored data obtained from a control sample, whereby a significantly different response pattern of the test sample as compared to the control sample is indicative of Alzheimer's disease; and (e) presenting the resulting information on a display or transmitting said information to a host computer using the processing unit.

* * * * *